United States Patent
Zribi et al.

(10) Patent No.: US 7,411,670 B2
(45) Date of Patent: Aug. 12, 2008

(54) COLLECTION PROBE FOR USE IN A RAMAN SPECTROMETER SYSTEM AND METHODS OF MAKING AND USING THE SAME

(75) Inventors: Anis Zribi, Rexford, NY (US); Ayan Banerjee, Bangalore (IN); Shivappa Ningappa Goravar, Karnataka (IN); Shankar (nmn) Chandrasekaran, Tamil Nadu (IN); Sandip Maity, Bangalore (IN); Glenn Scott Claydon, Wyantskill, NY (US); Stacey Joy Kennerly, Niskayuna, NY (US); Todd Ryan Tolliver, Clifton Park, NY (US); David Cecil Hays, Niskayuna, NY (US); Sheila Neumann Tandon, Niskayuna, NY (US); Long Que, Rexford, NY (US); Christopher Fred Keimel, Niskayuna, NY (US)

(73) Assignee: GE Homeland Protection, Inc., Newark, CA (US)

( * ) Notice: Subject to any disclaimer, the term of this patent is extended or adjusted under 35 U.S.C. 154(b) by 178 days.

(21) Appl. No.: 11/400,863

(22) Filed: Apr. 10, 2006

(65) Prior Publication Data

US 2007/0127019 A1    Jun. 7, 2007

Related U.S. Application Data

(60) Provisional application No. 60/748,327, filed on Dec. 7, 2005.

(51) Int. Cl.
*G01J 3/44* (2006.01)
(52) U.S. Cl. ..................... 356/301
(58) Field of Classification Search ................. 356/301
See application file for complete search history.

(56) References Cited

U.S. PATENT DOCUMENTS

| 5,615,008 A | 3/1997 | Stachelek |
| 2004/0207908 A1 | 10/2004 | Bastian et al. |
| 2004/0263843 A1* | 12/2004 | Knopp et al. ............... 356/301 |
| 2005/0283058 A1* | 12/2005 | Choo-Smith et al. ........ 600/315 |
| 2006/0006485 A1* | 1/2006 | Mouli ........................ 257/432 |

FOREIGN PATENT DOCUMENTS

| EP | 1471612 B1 | 6/2005 |
| WO | WO2006010367 A2 | 2/2006 |

OTHER PUBLICATIONS

Todd et al., "Deployment of a Fiber Bragg Grating-Based Measurement System in a Structural Health Monitoring Application", Smart Materials and Structures, www.lop.org/Journals/sm, vol. 10, pp. 534-539, 2001.

* cited by examiner

*Primary Examiner*—Kara E Geisel
(74) *Attorney, Agent, or Firm*—William E. Powell, III

(57) ABSTRACT

A photonic crystal based collection probe is provided. The probe includes a photonic crystal configured to guide and condition a beam of Raman scattered photons. Further, the device includes a spectrograph in optical communication with the photonic crystal and configured to receive Raman scattering from the photonic crystal. The device may be employed in a Raman spectrometer system.

21 Claims, 5 Drawing Sheets

COLLECTION PROBE FOR USE IN A RAMAN SPECTROMETER SYSTEM AND METHODS OF MAKING AND USING THE SAME

This non-provisional application claims the benefit of priority under 35 U.S.C. § 119(e) to U.S. Provisional Patent Application Ser. No. 60/748,327, filed Dec. 7, 2005, which is herein incorporated in its entirety by reference.

BACKGROUND

The invention relates generally to analytical systems. More particularly, the invention relates to a collection probe for use in a Raman spectrometer system.

The need for portable, rugged, high performance and low power analytical instruments is growing for a variety of defense and security applications where the ability to identify unknown substances is key. These expanding military needs require new instruments capable of detecting and resolving a large number of signatures from chemicals, biological analytes and mixtures thereof. These materials are potentially fluorescent as well as molecularly and structurally similar making identification very challenging. Given the danger posed by the presence of such biological and chemical agents in our immediate environment, whether in closed or open spaces, civilian areas or battlefields, it is imperative for such instruments to offer standoff and rapid detection capabilities as well as ruggedness to environmental conditions. This implies that minimal sample preparation is desirable and the analytical technique needs to be impervious to the presence of high percentage of water, immune to shock and vibrations and to numerous other environmental factors. Some of these desirable attributes are addressed by using Raman spectrometry. However, many of these capabilities, such as ruggedness and size still need to be addressed to make such a system portable and easier to be carried to inspection sites, rather than having to carry the sample back to the labs to be detected by these devices.

Photonic crystal based devices are employed for manipulating light in various ways. Typically, photonic crystal based optical devices with various functions including mirroring, waveguiding, splitting, collimation and spectral divergence are employed in analytical systems. While the implementation of these individual devices in a wide range of applications is very encouraging in demonstrating the capabilities of photonic crystals. Integrating the photonic crystal with other structures to form a practical optical system faces additional challenges. The integration of multiple optical components in these analytical systems employing photonic crystals require low loss optical couplers to transition the light between optical elements while maintaining polarization, mode profile with minimal scattering losses. Additionally, the fabrication processes needed to deposit, pattern, and etch these devices need to be highly integrated to enable multiple device and structure formation with the precision and accuracy necessary for device performance.

There exists a need for a collection probe for use in a portable analytical Raman system, which is integrated, compact and rugged.

SUMMARY

Figure 1:
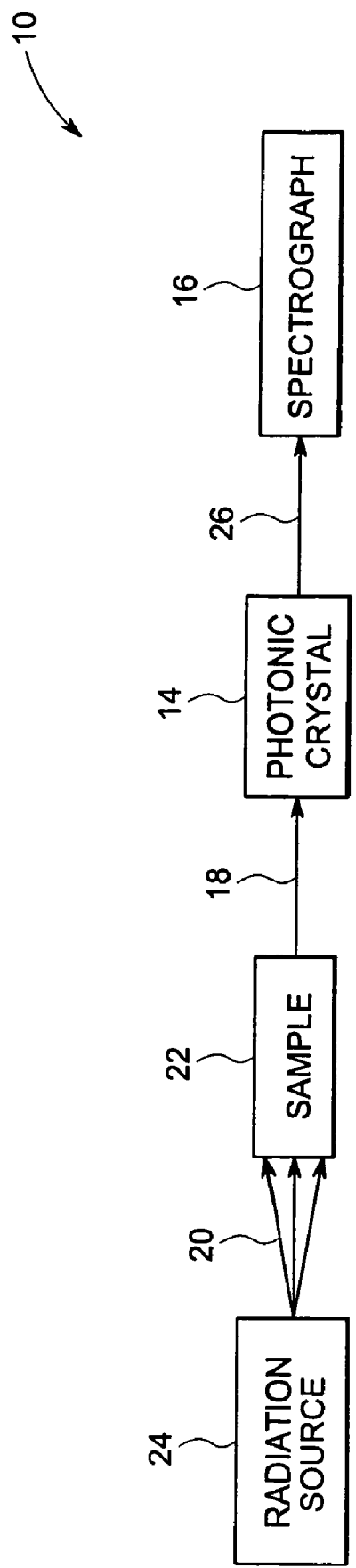
FIG. 1 is a diagrammatical illustration of a Raman spectrometer system employing a photonic crystal based collection probe in accordance with an exemplary embodiment of the invention.

Embodiments of the invention are directed to a photonic crystal based collection probe for use in a Raman spectrometer system, and a method of using the device.

One exemplary embodiment of the invention is a photonic crystal based collection probe. The probe includes a photonic crystal configured to guide Raman scattering. Further, the probe includes a spectrograph in optical communication with the photonic crystal and configured to receive Raman scattering from the photonic crystal.

Another exemplary embodiment of the invention is a Raman spectrometer system. The system includes an electromagnetic radiation source configured to direct electromagnetic radiation on a sample. The sample is configured to interact with the electromagnetic radiation to convert at least a portion of the electromagnetic radiation into Raman scattering and Rayleigh scattering. The system further includes a photonic crystal configured to focus the Raman scattering, and a spectrograph configured to receive the Raman scattering focused from the photonic crystal.

Another exemplary embodiment of the invention is a method of analyzing a sample in an analytical system. The method includes emitting incident electromagnetic radiation to a sample in a chamber to generate a response, wherein the response comprises Raman scattering and Rayleigh scattering. The method further includes focusing at least a portion of the Raman scattering through a photonic crystal, filtering the Rayleigh scattering from the response, and receiving the portion of the Raman scattering at a spectrograph to generate electrical signals proportional to one or more of a physical, a chemical, or a biological signature of the sample.

These and other advantages and features will be more readily understood from the following detailed description of preferred embodiments of the invention that is provided in connection with the accompanying drawings.

DETAILED DESCRIPTION OF EXEMPLARY EMBODIMENTS

In a typical Raman spectroscopy measurement, a sample is probed with intense monochromatic light (usually laser) resulting in elastic (Rayleigh scattering) and inelastic (Raman scattering) scattering of photons. Elastically scattered photons are at the same wavelength as the probing light and do not exchange energy with the sample molecules. These photons do not contribute to the Raman Spectroscopy studies. However, inelastically scattered photons or Raman photons are either red (stokes) or blue shifted (anti stokes) and carry information about the identity of the material as well as its chemical and physical structure. Raman scattered signal is about $10^6$ to about $10^8$ times weaker than Rayleigh scattered signal. Therefore, the broadband signal having the Raman and Rayleigh signal is broken down to its spectral components by a spectrograph, and the light intensity at each wavelength is analyzed by a photodetector.

In conventional systems, before the light reaches the spectrograph, the scattered photons are collected by high numerical aperture optics and the beam is focused, collimated and stripped of the strong signal, that is, the Rayleigh scattering, by using various optical elements present outside the chip having the spectrograph. However, connection to external off-chip optical elements, such as light sources, detectors, spectrographs, is usually a demanding task, requiring precise alignment between the sample handling chips and for example, optical fibers connecting chip with the off-chip optical elements. The lack of precise alignment may result in loss of already weak Raman signal, which may make it difficult to detect the optical responses from the sample. However, while employing photonic crystals these beam-conditioning functions may be met with a single device, while providing efficient device-to-device coupling and reduced optical losses. Further, photonic crystals may be integrated to fulfill functions such as filtering, focusing, collimation and guiding of light in a compact, low loss photon spectrometer for Raman system on a chip (RSC) as described below with regard to FIGS. 1-4.

Referring now to FIG. 1, a system 10 employing a photonic crystal based collection probe having a photonic crystal 14 and a spectrograph 16 is illustrated. Raman scattering 18 is generated as a result of radiation 20 being incident on a sample 22 by a radiation source 24, such as a laser. The photonic crystal 14 is configured to focus the Raman scattering or the Raman scattered photons 18 into radiation 26, which is then guided into the spectrograph 16. Further, as will be described in detail with regard to FIG. 2, additional photonic crystals may be employed to collimate, filter, or enhance reflectance of the Raman scattered photons 18. The spectrograph 16 is in optical communication with the photonic crystal 14. Further, the spectrograph 16 is configured to receive the radiation 26 from the photonic crystal 14. The system 10 may be employed in a Raman spectrometer system for analytical applications as will be described in detail with regard to FIG. 4.

Figure 5:
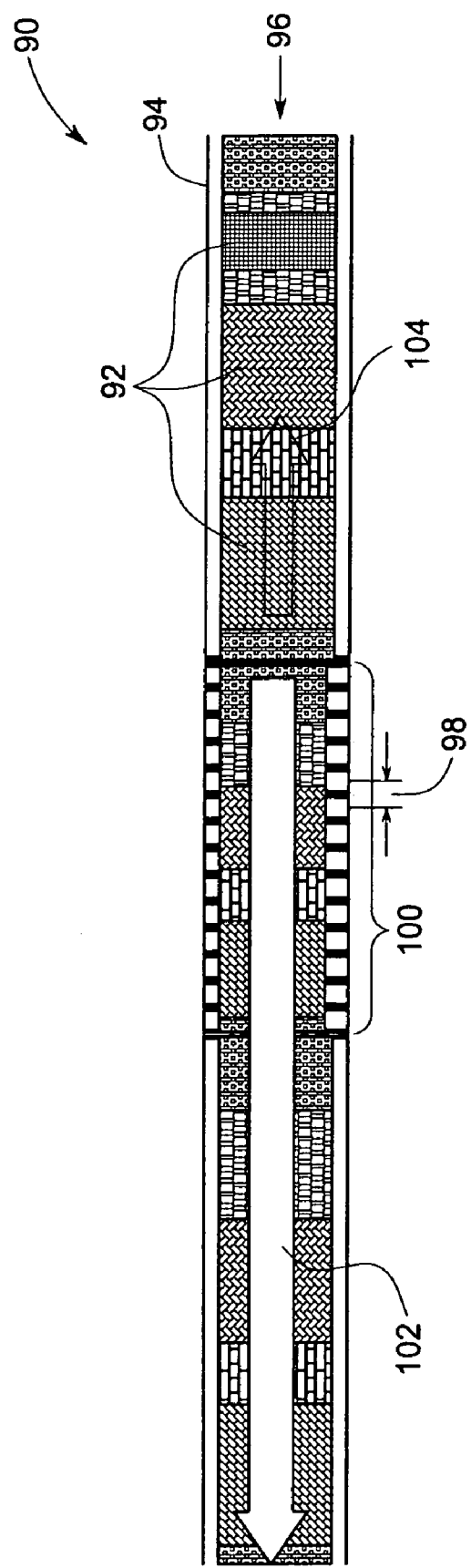
FIG. 5 is a cross-sectional view of an exemplary fiber Bragg grating for use in conjunction with a photonic crystal based collection probe in accordance with an exemplary embodiment of the invention.

It should be appreciated that a photonic crystal controls the propagation of light through a material by affecting the characteristics of the wave-vector (or k-vector). The photonic crystal is a structure composed of a periodic variation in the index of refraction such that the period is of the order of the wavelength of light as illustrated in FIG. 5. This periodicity may be created in one, two, or three dimensions where the complexity of the structure increases with dimension. Light traveling through the periodic structure of a photonic crystal may experience allowed and disallowed modes of propagation. The disallowed modes are those for which light in a photonic crystal cannot exist. These disallowed modes or "band gaps" in light propagation make photonic crystals desirable structures for manipulating light such as bending light by 90 degrees, reflecting broad spectra with low loss, collimating light without guiding structures, or dispersing multiple wavelengths with exceptionally divergent directions.

Propagation effects are often modeled using "equi-frequency surfaces" which are calculated with an eigen-frequency solver. An equi-frequency surface maps out the allowed wave-vectors for all spatial orientations within a structure at a constant frequency. These surfaces may be engineered to make photonic crystals. For example, a photonic crystal "superprism" may use low curvature regions of an equi-frequency surface to create a large angular sweep of an output beam for a small angular change in an input beam. At the same time, another photonic crystal effect known as "super-collimation" utilizes equi-frequency surfaces such that light experiences propagation with little or no divergence in the beam width for centimeter length scales. With a low curvature equi-frequency surface, the photonic crystal forces the group velocity, and therefore the direction of energy propagation, to be constant so that collimation is achieved even for a tightly focused input beam. This effect may be utilized for coupling the photonic crystal into the Fabry-Perot cavity.

Further, employing photonic crystals in the photonic crystal based collection probe may also enable integration of narrow-band tunable notch filters, sub-wavelength optical gratings, high-resolution MEMS Fabry-Perot devices tunable over broad spectral bands, broadband collimators and focusing devices in these analytical devices. Thereby improving the instrument ruggedness originating from fewer optical interconnects between the various components, which usually contribute to majority of optical loss in designs of portable Raman instruments. Additionally, the photonic crystal 14 and the spectrograph 16 may be fabricated on a single chip to have a short distance between the photonic crystal 14 and the spectrograph 16 as compared to devices having off-chip optical devices coupled to each other. The short distances of the order of few micrometer over which the optical signals may be routed in these devices, provide an additional miniaturization and enable formation of a Raman spectrometer system having a fully integrated Raman system on a chip (RSC). The Raman spectrometer system provides an integrated, compact and rugged analytical systems. Also, the collection probe may be employed in a portable Raman spectrometer system, which allows for on site analysis with little or no sample preparation. Accordingly, in defense applications the Raman spectrometer system may be carried to the site to detect any biological warfare agents instantly, without having to carry the samples to the lab for analysis, which is time consuming and causes unnecessary delay.

The sample 22 may be housed in a sample chamber (not shown). In one embodiment, the sample chamber may include a microfluidic channel or a waveguide. While employing the microfluidic chambers, the sample chamber may also include reaction chambers, sample mixers or pumps. The sample 22 may be disposed in a liquid or a gas environment. For example, the sample 22 may be disposed in a liquid environment having an organic composition, an aqueous medium, or both. Alternatively, the sample 22 may be disposed in a gaseous environment.

In one embodiment, the spectrograph 16 may include Micro Electro Mechanical Systems (MEMS). In one embodiment, the photonic crystal 14 may collimate and couple a broadband light having a wavelength in a range of from about 980 nanometers to about 1300 nanometers into a spectrograph such as a fixed Fabry Perot cavity.

Figure 2:
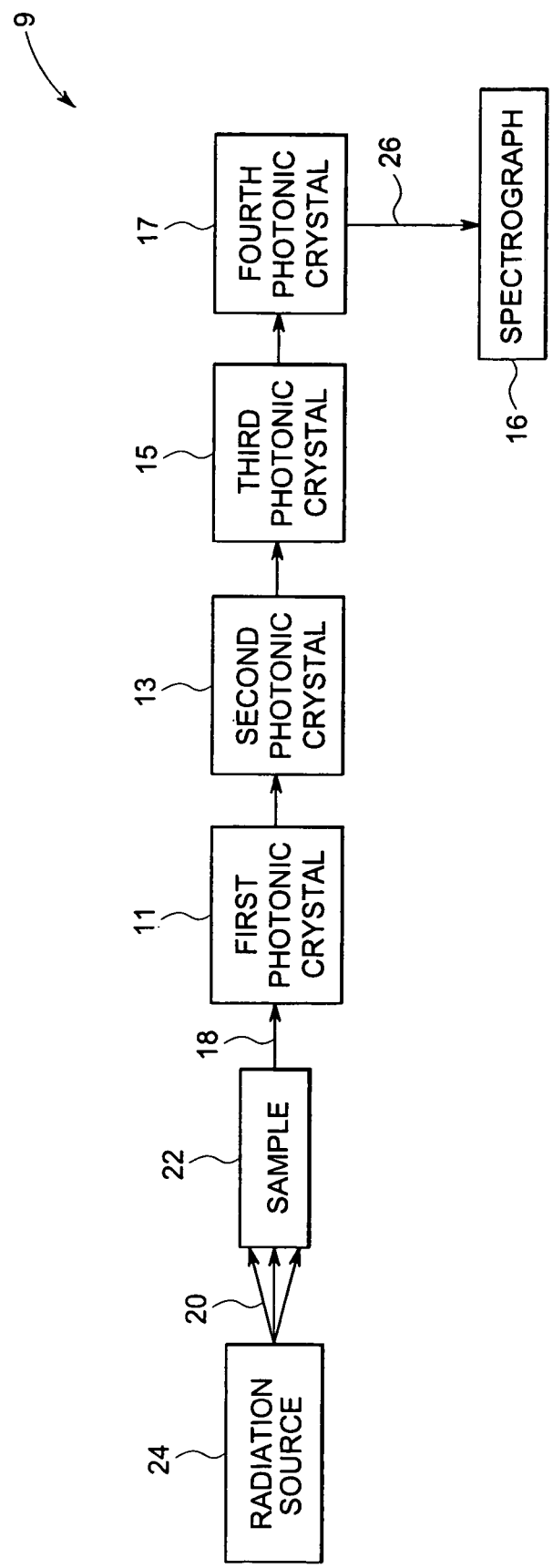
FIG. 2 is a diagrammatical illustration of a Raman spectrometer system employing a photonic crystal based collection probe in accordance with an exemplary embodiment of the invention.

As illustrated in FIG. 2, in one embodiment of the invention, more than one photonic crystal may be employed in a photonic crystal based collection probe employed in the system 9 to perform functions other than focusing the Raman scattered photons 18. For example, in the illustrated embodiment, a first photonic crystal 11 may be employed to focus the Raman scattered photons 18. A second photonic crystal 13 may be positioned such that the focused beam coming out of the first photonic crystal 11 is received by the second photonic crystal 13, which then collimates the beam. Further, a third photonic crystal 15 may be employed to filter the Rayleigh scattering from the focused and collimated beam, in this embodiment the notch filter, which is otherwise used for filtering out Rayleigh scattering from conventional analytical systems may not be required, thereby drastically reducing the cost of the device. Further, a fourth photonic crystal 17 may be employed to enhance reflectance of a tunable MEMS filter used as a spectrograph. It should be noted that depending on the functions, one or more of the photonic crystals 11, 13, 14, 15 or 17 may be employed in different combinations. For example, in a collection probe a combination of the photonic crystals 11 and 13 or 14 and 13 may be employed to obtain a beam, which is focused and relatively free of Raleigh scattering 18. In another example, if a separate filter, such as a fiber Bragg grating, is employed to filter out the Rayleigh scattering 18, the photonic crystal 11, or photonic crystal 14, or a combination of the photonic crystals 11 and 13, or 14 and 13 may be employed to focus and collimate the beam. In such an embodiment, the third photonic crystal 15 may not be required to filter out the Rayleigh scattering. Additionally, it should be noted that the photonic crystals may not necessarily be employed in the same sequence as illustrated in FIG. 2. Further, a microelectromechanical system (MEMS) tunable spectrometer may be used for spectroscopic applications such as Raman, infrared (IR) absorption etc.

Figure 3:
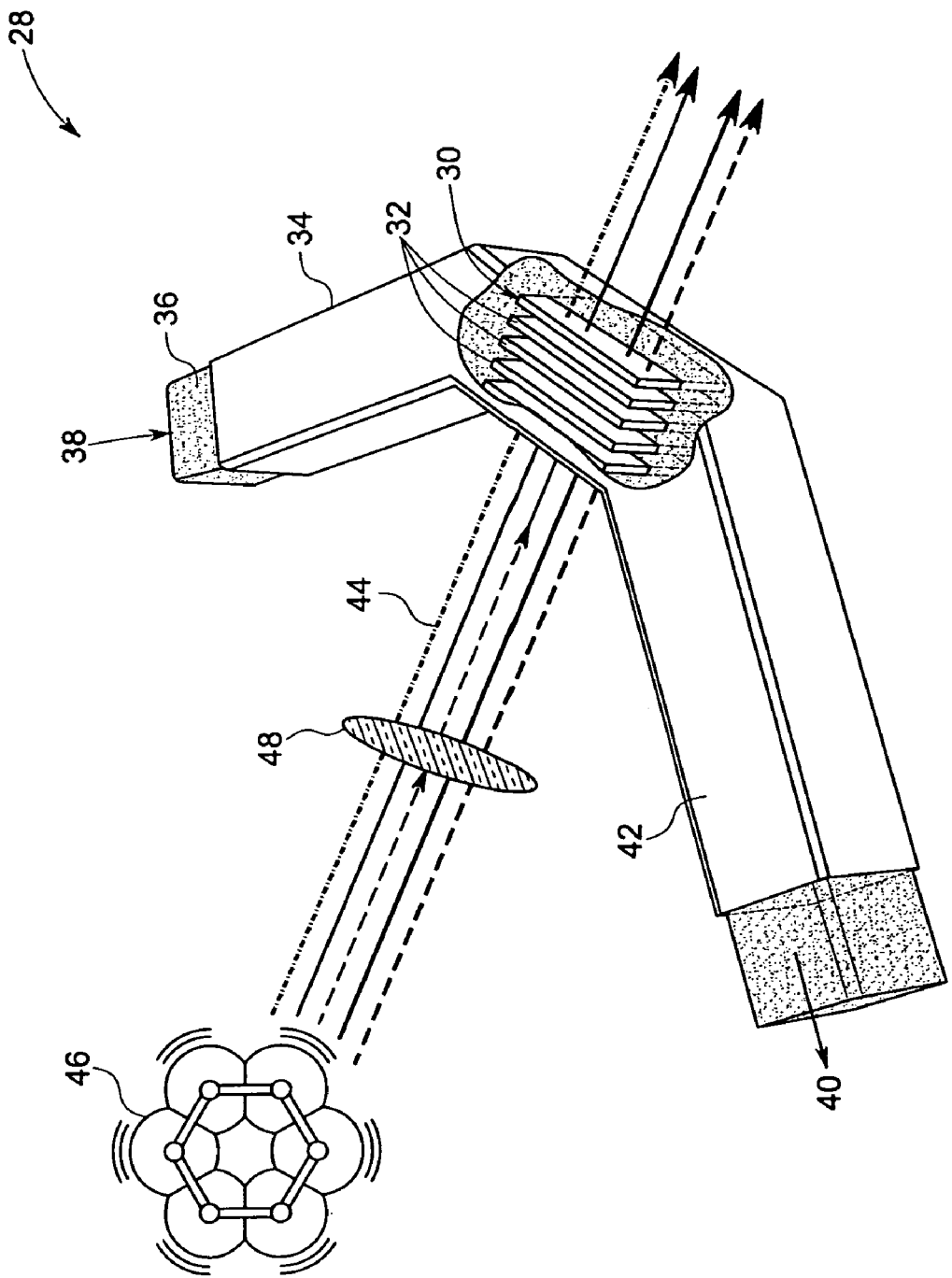
FIG. 3 is a perspective view of an exemplary photonic crystal based collection probe employing a photonic crystal disposed in a microfluidic channel in accordance with an exemplary embodiment of the invention.

As illustrated in FIG. 3, the system 28 includes a photonic crystal 30 having a plurality of 1-dimensional (1-D) parallel plates 32 housed inside a microfluidic channel 34. The microfluidic channel 34 includes a fluidic medium 36 disposed in between any two of the plurality of plates 32. It should be noted that the plurality of plates 32 along with the fluidic medium 36 disposed between the plurality of plates 32 constitute the photonic crystal 30. In one embodiment, the fluidic medium 36 having a refractive index $n_1$ may be introduced between the plates 32. It should be noted that the properties of the photonic crystal 30 may be tuned and/or altered by replacing the fluidic medium 36 with another fluidic medium (not shown) having a refractive index other than $n_1$. Therefore, the photonic crystal 30 housed inside the microfluidic channel 34 may be used as a microfluidic tunable filter. Further, the fluidic medium 36 may be introduced into the microfluidic channel 34 through the inlet 38 and taken out of the microfluidic channel 34 through the outlet 40.

The outer cladding 42 is transparent to the radiation 44 having Raman scattering emitted by the sample molecule 46. Optionally, an optical lens 48 may be employed to focus the radiation 44 into a location of the microfluidic channel 34 having the photonic crystal 30 disposed therein.

In one embodiment, a Raman spectrometer system employing a photonic crystal based collection probe may include one or more monochromatic excitation sources, light collection optics, guiding optics, collimating and focusing optics, a tunable filter, a photodetector, acquisition electronics, conditioning electronics and device controllers. Optionally, the spectrometer system may include an optical power management system to avoid sample burning. For example, the Raman spectrometer system may include a collimator, a tunable cavity length Fabry-Perot and a routing mechanism, such as a waveguide or an optical fiber, to enable communication between these two devices with low coupling loss. As a result a chip that monolithically integrates input coupling, pump wavelength rejection, collimation, and routing in a small form factor for a Raman system may be designed.

Figure 4:
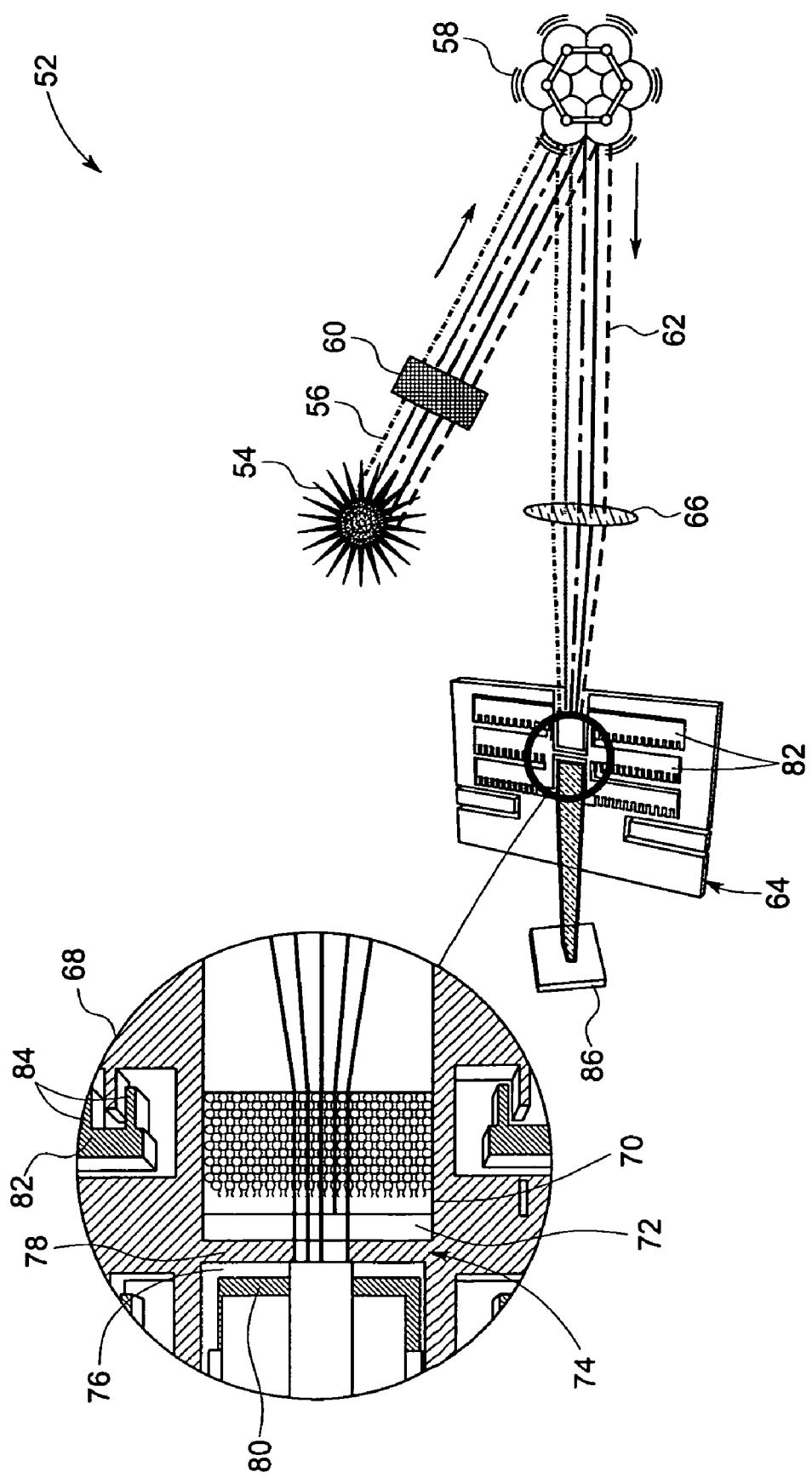
FIG. 4 is a diagrammatical illustration of an exemplary Raman spectrometer system in accordance with an exemplary embodiment of the invention.

FIG. 4 shows an exemplary device 52 configured to be employed in a Raman spectrometer system design. The device 52 includes a laser source 54 that emits monochromatic radiation 56 for exciting a sample 58. The device 52 may employ more than one laser sources emitting monochromatic lights at different wavelengths. The device 52 may include an optical power management module 60. The module 60 may be desirable in instances where the sample 58 is temperature sensitive. Also, the module 60 may be employed to control the laser power to prevent sample 58 from burning. The module 60 may include, for example a shutter.

Upon interaction with the radiation 56, the molecules of the sample 58 vibrate due to excitation, thereby giving out signature radiation 62 which contains either red (stokes) or blue shifted (anti stokes) photons that carry information about the identity of the sample 58 as well as its chemical and physical structures. The radiation 62 includes a combination of Raman and Rayleigh scattering. Optionally, collection optics, such as an optical lens 66 may be positioned between the sample 58 and the RSC 64 to receive the radiation 62 from the sample 58 and direct the radiation 62 to the RSC 64. A photonic crystal (not shown) may be used in place of the optical lens 66. The radiation 62 may be then collimated and filtered by using optical devices of the Raman spectrometer chip RSC 64.

An enlarged view of a portion 68 of the RSC 64 illustrates the collimation and filtering functions in detail. The portion 68 includes a photonic crystal collimator 70 having a taper configured therein to collimate the radiation 62. Further, the dominating Rayleigh scattering component of the radiation 66 at the optical source wavelength is filtered out by using a photonic crystal collimator 70. Alternatively, a fiber Bragg grating (not shown) or sub-wavelength optical grating may be employed to filter out the Rayleigh scattering. The fiber Bragg grating may be either employed in combination with the photonic crystal collimator 70, or may be employed independent of the photonic crystal collimator 70. When employed in combination with the photonic crystal collimator 70, the fiber Bragg grating may replace the photonic crystal filter 72, which is used to perform a similar function of filtering out the Rayleigh scattering. Similar to the function of the fiber Bragg grating, a sub-wavelength grating may be employed to reflect the Rayleigh scattering that is the same wavelength of the excitation source. The sub-wavelength grating may be a separate element or formed directly in or on the substrate material of the integrated photonic crystal elements. Optical thin film waveguide material may be combined with the sub-wavelength grating to reflect the incident Rayleigh scattering while coupling the Raman signal into an in-plane optical waveguide.

The portion 68 of the RSC 64 further includes a tunable Fabry-Perot filter 74 as a spectrograph to detect the component Raman scattering. The tunable Fabry-Perot filter 74 includes a resonant cavity 76 defined by two mirrors 78 and 80. One of the mirrors 78 or 80 may be stationary at one position and the other one may be movable, thereby facilitating the tuning or changing of the wavelength of the light transmitted through the cavity 76. The mirrors 78 and 80 may be either both flat or both curved, or one flat and one curved. When broadband light is coupled to the cavity 76, multiple internal reflections and refractions occur and interference between transmitted beams takes place. At specific distances between the two mirrors interference is constructive and interference is pattern is produced on the other end of the Fabry-Perot. The central peak (main mode of the cavity at a specific distance between the mirrors) is a high intensity peak and the transmitted light is monochromatic. The motion of the other mirror to adjust the wavelength of the transmitted light through the cavity may be facilitated by actuator combs 82. The protrusions 84 of the actuator combs may be locked with the mirror, for example 80, of the tunable Fabry-Perot filter 74 to slide the mirror 80 along the RSC 64 and cause the transmitted wavelength of the tunable Fabry-Perot filter 74 to be altered.

The photonic crystal collimator 70 may be one dimensional (1D), two-dimensional (2D) or three dimensional (3D). One-dimensional (1D) photonic crystals may be relatively simple to fabricate and are often used as mirror structures where the bandwidth of reflectivity is determined by the index contrast between mirror layers. 2D photonic crystals allow greater functionality, but there is a trade-off between having greater functionality and fabrication complexity. For example, 2D planar photonic crystals may enable 90-degree bends, waveguides, splitters, collimators, and prisms for light manipulation. Fabrication of the required sub-micron feature sizes is often implemented with conventional planar fabrication techniques. Various patterning and fabrication techniques exist that enable sub-micron feature formation.

Photonic crystals that operate in the infrared red (IR) regime require lattice constants much less than 1 micrometer. Typically such a structure may contain a periodic lattice composed of etched holes in silicon or silicon dioxide. These lattice structures are designed with features in the range of about 200 nanometers to about 300 nanometers, but spacing between such structures may be less than about 100 nanometers. Accurately patterning dimensions on this length scale requires nanofabrication methods. Technologies such as electron beam lithography (EBL), extreme ultra violet lithography (EUVL), imprint lithography, interference lithography and self assembly based techniques are non-limiting examples of fabrication technologies that may be employed for patterning. These patterning techniques may enable control over minimum feature size, alignment, feature proximity effects, fabrication costs, yield, time to fabricate, maximum pattern-able area, pattern flexibility, and pattern adaptability. Deep reactive ion etching (DRIE) may be employed for uniform pattern transfer of high aspect ratio nanostructures integrated with micro-scale features.

In one embodiment, a combination of a deep RIE process and a KOH-based wet etching process to fabricate high aspect ratio (up to about 100) silicon structures. In order to improve the optical finish of the sidewall mirror, DRIE and KOH wet etching may be combined, to reduce the surface roughness to about 10 nanometers level.

After defining the patterns through e-beam lithography, a unique combination of various fabrication techniques such as, but not limited to, reactive ion etching, e-beam evaporation and photolithography may be employed to transfer the multilayered micro and photonic crystal pattern into the thin films and substrate. Different fabrication approaches may be employed to achieve the same. For example, one approach may include patterning the structure (micro and nano features) though electron beam lithography. Advantageously, this approach uses a single resist exposure for features at all length scales thus negating the need to align electron beam lithography written nanostructures with optical lithography defined microstructures. However, this technique requires increased write time as well as being confined to a maximum patternable area of about 200 micrometers×200 micrometers due to restriction on the electron optics. A second approach may use optical lithography to define the Fabry Perot microstructures, align the sub-micron photonic crystal structures to the Fabry Perot and write in the nanostructures using electron beam lithography. This technique is advantageous if the overall device structure is few hundreds of micrometers in size. However, the added alignment technique may induce some mismatch that may result in signal loss.

The resolution of the Fabry-Perot filter 74 has a significant effect on the overall resolution of the micro-instrument and may be in certain cases the limiting factor. For example, equation. 1 is an expression of the Fabry-Perot resolution in terms of the velocity of light (c), the refractive index of the medium in the cavity (n), the cavity length (L), the angle of incidence of the light beam inside the cavity (θ) and the total finesse (F) of the cavity. It should be noted that the finesse of the cavity is defined as its free spectral range divided by the (full width at half maximum) bandwidth of its resonances. It is fully determined by the cavity losses and is independent of the cavity length.

$$\Delta v = \frac{c}{2nFL\cos\theta} \qquad \text{Equation 1}$$

As seen from equation 1, as the angle of incidence of the incoming beam deviates from 0° relative to the normal of the Fabry Perot mirrors, the device and hence the Raman spectrometer system resolution may degrade. Therefore, it is desirable to minimize the incoming beam divergence at it gets coupled into the Fabry-Perot cavity. This may be achieved by positioning a point source in the focal plane of an illuminating lens. To approach the ideal case (0° between the incident beam and the mirror normal), a pinhole may be used to approximate the point source. Because the light throughput of the instrument is proportional to the pinhole area it is advantageous to maximize this parameter for better signal to noise ratio (SNR). However, this may result in increasing the beam divergence and hence broadening the Fabry-Perot peaks indicating a degradation of the spectrograph resolution. Therefore, it may not be amenable for miniaturization beyond a certain point, where throughput and diffraction issues become prevalent. However, using planar, integrated photonic crystal devices may eliminate the need for trading off throughput for beam collimation, thereby resulting in higher resolution of the micro instruments.

Further, conventional methods for guiding light into the cavity, such as single-mode or multimode optical fiber, usually result in a significant loss in resolution. The half-angle numerical aperture of single-mode and multimode fiber is 6 degrees and 11 degrees, respectively, which lead to divergent beams of the same angle. According to Equation 1, this results in a severe decrease in the resolution of the Fabry-Perot cavity compared to fully collimated light. Therefore, a photonic crystal collimator 70 may result in enhanced performance of such a device.

Further, a miniaturized detector 86 may be employed to detect the radiation 62 and generate corresponding signals. As opposed to conventional detection devices (e.g., charge coupled devices) that may require cooling, detector 86 may include a quantum dot detector array or an avalanche photodiode detector (APD), for example. The detector 86 provides a higher signal-to-noise ratio (SNR), requires little to no cooling, and may provide digital fluorescence and Rayleigh line removal.

FIG. 5 depicts an exemplary embodiment of a fiber Bragg grating device 90. The fiber Bragg grating 90 may be employed for example in the RSC 64 of FIG. 4. As discussed above, the fiber Bragg grating 90 may be employed to reflect the Rayleigh scattering that is at the same wavelength as the excitation source, such as excitation source 54 of FIG. 4. The fiber Bragg grating 90 includes portions 92 having different refractive index patterns and arranged in a predetermined fashion. The portions 92 may be disposed in the core 96 of an optical fiber 94. The portions 92 may be formed by exposing the optical fiber 94 to a pre-designed interference pattern (not shown). In one embodiment, the optical fiber 94 is a germanium doped silica fiber. In one embodiment, the diameter of the fiber 94 is about 50 micrometers. The pitch 98 of the grating 100 may be adjusted such that the reflected wavelength 102 is the wavelength of the excitation source, and the rest of the wavelength (Raman scattering) 104 is allowed to pass through the fiber Bragg grating 90. If the wavelength of the excitation source, such as source 54 of FIG. 4, is about 980 nanometers, the pitch 98 or the grating period is about 330 nanometers, thereby resulting in a reflected wavelength 102 of about 980 nanometers. In one embodiment, the reflection efficiency for a particular wavelength is in a range of from about 80 percent to about 100 percent. The reflection wavelength may be tuned by changing the pitch 98 of the grating 100. In one embodiment, the pitch may be tuned by controlling the temperature of the fiber by using a heating element.

The use of photonic crystals in the passive optics of the RSC facilitates high quality miniature optics amenable to a high degree of integration. As a result of the integration of the spectroscopy components into a microsystem, the Raman spectrometer is portable, light, miniature (e.g., the size of a remote control or smaller), autocalibrated, high-resolution (e.g., better than 5 $cm^{-1}$) and offers rapid, quantitative identification of bio and chemical analytes in gas, liquid and solid phases. This spectrometer may thus be used in applications as diverse as: rapid narcotics and explosives identification, water quality monitoring, just in time drug identification, blood analyte measurement, etc.

Further, depending on the precise and accurate semiconductor techniques used to fabricate the photonic crystals, the aberration issues typically encountered in standard optical components (e.g. astigmatism), may be significantly reduced while allowing dramatic size reduction of up to about the 1000 times. Additionally, the RSC will enable near excitation-wavelength analysis (by designing the filter that may not filter out the wavelengths close to the excitation wavelength), higher resolution for mixture analyses (the spectrograph may be a tunable Fabry Perot which is designed to have a high resolution (15×)), higher signal to noise ratio (by lowering optical losses at the interconnects, shorter optical path, Fabry Perot spectrograph typically has a higher optical throughput than dispersive spectrographs, and by using enhancement techniques like SERS and optofluidics modules) (1011×), smaller footprint (10×), lighter weight (4×) and lower power dissipation (7×).

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while the photonic crystal based collection probe is described in conjunction with Raman spectrometer system, it should be appreciated that the photonic crystal based collection probe may find utility for any application in which a Raman spectrometer is employed. Additionally, while various embodiments of the invention have been described, it is to be understood that aspects of the invention may include some of the described embodiments. Accordingly, the invention is not to be seen as limited by the foregoing description, but is only limited by the scope of the appended claims.

What is claimed as new and desired to be protected by Letters Patent of the United States is:

1. A photonic crystal based collection probe, comprising:
    a photonic crystal configured to focus Raman scattered photons; and
    a spectrograph in optical communication with said photonic crystal and configured to receive Raman scattered photons from said photonic crystal.

2. The photonic crystal based collection probe of claim 1, wherein said spectrograph comprises a micro electro-mechanical system spectrograph.

3. The photonic crystal based collection probe of claim 2, wherein said spectrograph comprises a tunable Fabry-Perot filter.

4. The photonic crystal based collection probe of claim 1, further comprising a photonic crystal configured to collimate said Raman scattered photons.

5. The photonic crystal based collection probe of claim 1, further comprising a photonic crystal configured to enhance reflectance and finesse of a micro electro mechanical spectrograph.

6. The photonic crystal based collection probe of claim 1, further comprising a filter for Rayleigh scattering separation.

7. The photonic crystal based collection probe of claim 6, wherein the filter for Rayleigh scattering separation comprises a photonic crystal configured to filter Rayleigh scattered photons from said Raman scattered photons.

8. The photonic crystal based collection probe of claim 6, wherein said filter comprises a fiber Bragg grating device.

9. The photonic crystal based collection probe of claim 8, wherein a grating period of said fiber Bragg grating device is about 330 nanometers.

10. The photonic crystal based collection probe of claim 7, wherein a rejection efficiency of said filter is in a range of from about 80 percent to about 100 percent.

11. The photonic crystal based collection probe of claim 6, wherein said filter comprises a sub-wavelength optical grating.

12. A Raman spectrometer system, comprising:
    an electromagnetic radiation source configured to direct electromagnetic radiation on a sample, wherein said sample is configured to interact with said electromagnetic radiation to convert at least a portion of said electromagnetic radiation into Raman scattering and Rayleigh scattering;
    a photonic crystal configured to focus said Raman scattering; and
    a spectrograph configured to receive said Raman scattering focused from said photonic crystal.

13. The Raman spectrometer system as defined in claim 12, further comprising a fiber Bragg grating device disposed between said photonic crystal and said spectrograph.

14. The Raman spectrometer system as defined in claim 13, wherein said fiber Bragg grating device is configured to reject at least a portion of a radiation of predetermined wavelength.

15. The Raman spectrometer system as defined in claim 13, wherein said fiber Bragg grating device is coupled to a heater for altering a pitch of said fiber Bragg grating.

16. The Raman spectrometer system as defined in claim 12, wherein said sample is disposed in a microfluidic channel.

17. The Raman spectrometer system as defined in claim 12, wherein said photonic crystal is disposed in a microfluidic channel.

18. The Raman spectrometer system as defined in claim 12, further comprising a photonic crystal configured to filter Rayleigh scattering from said from said Raman scattering.

19. The Raman spectrometer system as defined in claim 18, wherein said photonic crystal is disposed in a microfluidic device.

20. The Raman spectrometer system as defined in claim 12, further comprising a photonic crystal configured to collimate said Raman scattering.

21. The Raman spectrometer system as defined in claim 12, further comprising a photonic crystal configured to enhance reflectance of photons of said Raman scattering.

* * * * *